(12) United States Patent
Lee et al.

(10) Patent No.: US 9,173,623 B2
(45) Date of Patent: Nov. 3, 2015

(54) X-RAY TUBE AND RECEIVER INSIDE MOUTH

(71) Applicant: Moxtek, Inc., Orem, UT (US)

(72) Inventors: Samuel Soonho Lee, Newton, MA (US); Victor Armando Tirado, Woburn, MA (US); David S. Crawford, Salem, UT (US)

(73) Assignees: Samuel Soonho Lee, Newton, MA (US); Moxtek, Inc., Orem, UT (US)

( * ) Notice: Subject to any disclaimer, the term of this patent is extended or adjusted under 35 U.S.C. 154(b) by 107 days.

(21) Appl. No.: 14/249,186

(22) Filed: Apr. 9, 2014

(65) Prior Publication Data

US 2014/0341346 A1 Nov. 20, 2014

Related U.S. Application Data

(60) Provisional application No. 61/814,144, filed on Apr. 19, 2013.

(51) Int. Cl.
*A61B 6/14* (2006.01)
*A61B 6/00* (2006.01)

(52) U.S. Cl.
CPC ............. *A61B 6/145* (2013.01); *A61B 6/4057* (2013.01); *A61B 6/425* (2013.01); *A61B 6/542* (2013.01)

(58) Field of Classification Search
CPC .......... A61B 6/14; A61B 6/145; A61B 6/587; A61B 6/4057; A61B 6/425; G01N 23/04; G01N 23/08; G01N 23/083; G03B 42/042
USPC .................................... 378/62, 168, 193, 205
See application file for complete search history.

(56) References Cited

U.S. PATENT DOCUMENTS

| | | | |
|---|---|---|---|
| 1,276,706 A | 8/1918 | Aydelotte | |
| 1,881,448 A | 10/1932 | Forde et al. | |
| 1,946,288 A | 2/1934 | Kearsley | |
| 2,291,948 A | 8/1942 | Cassen | |
| 2,316,214 A | 4/1943 | Atlee et al. | |
| 2,329,318 A | 9/1943 | Atlee et al. | |
| 2,340,363 A | 2/1944 | Atlee et al. | |

(Continued)

FOREIGN PATENT DOCUMENTS

| | | |
|---|---|---|
| DE | 1030936 | 5/1958 |
| DE | 4430623 | 3/1996 |

(Continued)

OTHER PUBLICATIONS

Barkan et al., "Improved window for low-energy x-ray transmission a Hybrid design for energy-dispersive microanalysis," Sep. 1995, 2 pages, Ectroscopy 10(7).

(Continued)

*Primary Examiner* — Jurie Yun
(74) *Attorney, Agent, or Firm* — Thorpe North & Western, LLP

(57) ABSTRACT

A method and a device for low x-ray radiation dosage while taking x-ray images of a patient's teeth is disclosed. The method includes use of an x-ray source and receiver positioned at least partially inside the patient's mouth. The device includes an x-ray source and receiver attached together by a bite holder and configured to both be disposed at least partially inside the patient's mouth across a tooth while taking x-ray images of a patient's tooth.

20 Claims, 8 Drawing Sheets

(56) References Cited

U.S. PATENT DOCUMENTS

| | | |
|---|---|---|
| 2,502,070 A | 3/1950 | Atlee et al. |
| 2,663,812 A | 12/1953 | Jamison et al. |
| 2,683,223 A | 7/1954 | Hosemann |
| 2,952,790 A | 9/1960 | Steen |
| 3,356,559 A | 12/1967 | Juras |
| 3,358,368 A | 12/1967 | Kuhnl |
| 3,397,337 A | 8/1968 | Denholm |
| 3,434,062 A | 3/1969 | Cox |
| 3,665,236 A | 5/1972 | Gaines et al. |
| 3,679,927 A | 7/1972 | Kirkendall |
| 3,691,417 A | 9/1972 | Gralenski |
| 3,741,797 A | 6/1973 | Chavasse, Jr. et al. |
| 3,751,701 A | 8/1973 | Gralenski et al. |
| 3,752,990 A | 8/1973 | Fischer |
| 3,801,847 A | 4/1974 | Dietz |
| 3,828,190 A | 8/1974 | Dahlin et al. |
| 3,851,266 A | 11/1974 | Conway |
| 3,872,287 A | 3/1975 | Koeman |
| 3,882,339 A | 5/1975 | Rate et al. |
| 3,894,219 A | 7/1975 | Weigel |
| 3,906,235 A | 9/1975 | Fischer |
| 3,962,583 A | 6/1976 | Holland et al. |
| 3,970,884 A | 7/1976 | Golden |
| 4,007,375 A | 2/1977 | Albert |
| 4,075,526 A | 2/1978 | Grubis |
| 4,100,417 A | 7/1978 | Goetzl et al. |
| 4,160,311 A | 7/1979 | Ronde et al. |
| 4,163,900 A | 8/1979 | Warren et al. |
| 4,178,509 A | 12/1979 | More et al. |
| 4,184,097 A | 1/1980 | Auge |
| 4,193,002 A | 3/1980 | Muether et al. |
| 4,200,795 A | 4/1980 | Kawamura et al. |
| 4,250,127 A | 2/1981 | Warren et al. |
| 4,293,373 A | 10/1981 | Greenwood |
| 4,368,538 A | 1/1983 | McCorkle |
| 4,393,127 A | 7/1983 | Greschner et al. |
| 4,400,822 A | 8/1983 | Kuhnke et al. |
| 4,421,986 A | 12/1983 | Friauf et al. |
| 4,443,293 A | 4/1984 | Mallon et al. |
| 4,463,338 A | 7/1984 | Utner et al. |
| 4,504,895 A | 3/1985 | Steigerwald |
| 4,521,902 A | 6/1985 | Peugeot |
| 4,532,150 A | 7/1985 | Endo et al. |
| 4,573,186 A | 2/1986 | Reinhold |
| 4,576,679 A | 3/1986 | White |
| 4,591,756 A | 5/1986 | Avnery |
| 4,608,326 A | 8/1986 | Neukermans et al. |
| 4,645,977 A | 2/1987 | Kurokawa et al. |
| 4,675,525 A | 6/1987 | Amingual et al. |
| 4,679,219 A | 7/1987 | Ozaki |
| 4,688,241 A | 8/1987 | Peugeot |
| 4,696,994 A | 9/1987 | Nakajima et al. |
| 4,705,540 A | 11/1987 | Hayes |
| 4,734,924 A | 3/1988 | Yahata et al. |
| 4,761,804 A | 8/1988 | Yahata |
| 4,777,642 A | 10/1988 | Ono |
| 4,797,907 A | 1/1989 | Anderton |
| 4,818,806 A | 4/1989 | Kunimune et al. |
| 4,819,260 A | 4/1989 | Haberrecker |
| 4,862,490 A | 8/1989 | Karnezos et al. |
| 4,870,671 A | 9/1989 | Hershyn |
| 4,876,330 A | 10/1989 | Higashi et al. |
| 4,878,866 A | 11/1989 | Mori et al. |
| 4,885,055 A | 12/1989 | Woodbury et al. |
| 4,891,831 A | 1/1990 | Tanaka et al. |
| 4,933,557 A | 6/1990 | Perkins et al. |
| 4,939,763 A | 7/1990 | Pinneo et al. |
| 4,957,773 A | 9/1990 | Spencer et al. |
| 4,960,486 A | 10/1990 | Perkins et al. |
| 4,969,173 A | 11/1990 | Valkonet |
| 4,979,198 A | 12/1990 | Malcolm et al. |
| 4,979,199 A | 12/1990 | Cueman et al. |
| 4,995,069 A | 2/1991 | Tanaka |
| 5,010,562 A | 4/1991 | Hernandez et al. |
| 5,060,252 A | 10/1991 | Vogler et al. |
| 5,063,324 A | 11/1991 | Grunwald |
| 5,066,300 A | 11/1991 | Isaacson et al. |
| 5,077,771 A | 12/1991 | Skillicorn et al. |
| 5,077,777 A | 12/1991 | Daly |
| 5,090,046 A | 2/1992 | Friel |
| 5,105,456 A | 4/1992 | Rand et al. |
| 5,117,829 A | 6/1992 | Miller et al. |
| 5,153,900 A | 10/1992 | Nomikos et al. |
| 5,161,179 A | 11/1992 | Suzuki et al. |
| 5,173,612 A | 12/1992 | Imai et al. |
| 5,178,140 A | 1/1993 | Ibrahim |
| 5,187,737 A | 2/1993 | Watanabe |
| 5,196,283 A | 3/1993 | Ikeda et al. |
| 5,200,984 A | 4/1993 | Laeuffer |
| 5,217,817 A | 6/1993 | Verspui et al. |
| 5,226,067 A | 7/1993 | Allred et al. |
| RE34,421 E | 10/1993 | Parker et al. |
| 5,258,091 A | 11/1993 | Imai et al. |
| 5,267,294 A | 11/1993 | Kuroda et al. |
| 5,343,112 A | 8/1994 | Wegmann et al. |
| 5,347,571 A | 9/1994 | Furbee et al. |
| 5,391,958 A | 2/1995 | Kelly |
| 5,400,385 A | 3/1995 | Blake et al. |
| 5,422,926 A | 6/1995 | Smith et al. |
| 5,428,658 A | 6/1995 | Oettinger et al. |
| 5,469,429 A | 11/1995 | Yamazaki et al. |
| 5,469,490 A | 11/1995 | Golden et al. |
| 5,478,266 A | 12/1995 | Kelly |
| 5,521,851 A | 5/1996 | Wei et al. |
| 5,524,133 A | 6/1996 | Neale et al. |
| 5,532,003 A | 7/1996 | Wong et al. |
| RE35,383 E | 11/1996 | Miller et al. |
| 5,571,616 A | 11/1996 | Phillips et al. |
| 5,578,360 A | 11/1996 | Viitanen |
| 5,592,042 A | 1/1997 | Takuchi et al. |
| 5,607,723 A | 3/1997 | Plano et al. |
| 5,621,780 A | 4/1997 | Smith et al. |
| 5,627,871 A | 5/1997 | Wang |
| 5,631,943 A | 5/1997 | Miles |
| 5,673,044 A | 9/1997 | Pellon |
| 5,680,433 A | 10/1997 | Jensen |
| 5,682,412 A | 10/1997 | Skillicorn et al. |
| 5,696,808 A | 12/1997 | Lenz |
| 5,706,354 A | 1/1998 | Stroehlein |
| 5,729,583 A | 3/1998 | Tang et al. |
| 5,774,522 A | 6/1998 | Warburton |
| 5,812,632 A | 9/1998 | Schardt et al. |
| 5,835,561 A | 11/1998 | Moorman et al. |
| 5,870,051 A | 2/1999 | Warburton et al. |
| 5,898,754 A | 4/1999 | Gorzen |
| 5,907,595 A | 5/1999 | Sommerer |
| 5,978,446 A | 11/1999 | Resnick |
| 6,002,202 A | 12/1999 | Meyer et al. |
| 6,005,918 A | 12/1999 | Harris et al. |
| 6,044,130 A | 3/2000 | Inazura et al. |
| 6,062,931 A | 5/2000 | Chung et al. |
| 6,069,278 A | 5/2000 | Chuang |
| 6,073,484 A | 6/2000 | Miller et al. |
| 6,075,839 A | 6/2000 | Treseder |
| 6,097,790 A | 8/2000 | Hasegawa et al. |
| 6,129,901 A | 10/2000 | Moskovits et al. |
| 6,133,401 A | 10/2000 | Jensen |
| 6,134,300 A | 10/2000 | Trebes et al. |
| 6,184,333 B1 | 2/2001 | Gray |
| 6,205,200 B1 | 3/2001 | Boyer et al. |
| 6,277,318 B1 | 8/2001 | Bower et al. |
| 6,282,263 B1 | 8/2001 | Arndt et al. |
| 6,288,209 B1 | 9/2001 | Jensen |
| 6,307,008 B1 | 10/2001 | Lee et al. |
| 6,320,019 B1 | 11/2001 | Lee et al. |
| 6,351,520 B1 | 2/2002 | Inazaru |
| 6,385,294 B2 | 5/2002 | Suzuki et al. |
| 6,388,359 B1 | 5/2002 | Duelli et al. |
| 6,438,207 B1 | 8/2002 | Chidester et al. |
| 6,477,235 B2 | 11/2002 | Chornenky et al. |
| 6,487,272 B1 | 11/2002 | Kutsuzawa |
| 6,487,273 B1 | 11/2002 | Takenaka et al. |
| 6,494,618 B1 | 12/2002 | Moulton |
| 6,546,077 B2 | 4/2003 | Chornenky et al. |

(56) References Cited

U.S. PATENT DOCUMENTS

| | | | |
|---|---|---|---|
| 6,567,500 B2 | 5/2003 | Rother |
| 6,644,853 B1 | 11/2003 | Kantor et al. |
| 6,645,757 B1 | 11/2003 | Okandan et al. |
| 6,646,366 B2 | 11/2003 | Hell et al. |
| 6,658,085 B2 | 12/2003 | Sklebitz |
| 6,661,876 B2 | 12/2003 | Turner et al. |
| 6,740,874 B2 | 5/2004 | Doring |
| 6,778,633 B1 | 8/2004 | Loxley et al. |
| 6,799,075 B1 | 9/2004 | Chornenky et al. |
| 6,803,570 B1 | 10/2004 | Bryson, III et al. |
| 6,803,571 B1 | 10/2004 | Mankos et al. |
| 6,816,573 B2 | 11/2004 | Hirano et al. |
| 6,819,741 B2 | 11/2004 | Chidester |
| 6,838,297 B2 | 1/2005 | Iwasaki et al. |
| 6,852,365 B2 | 2/2005 | Smart et al. |
| 6,853,568 B2 | 2/2005 | Li et al. |
| 6,866,801 B1 | 3/2005 | Mau et al. |
| 6,876,724 B2 | 4/2005 | Zhou et al. |
| 6,944,268 B2 | 9/2005 | Shimono |
| 6,956,706 B2 | 10/2005 | Brandon |
| 6,962,782 B1 | 11/2005 | Livache et al. |
| 6,976,953 B1 | 12/2005 | Pelc |
| 6,987,835 B2 | 1/2006 | Lovoi |
| 7,035,379 B2 | 4/2006 | Turner et al. |
| 7,046,767 B2 | 5/2006 | Okada et al. |
| 7,049,735 B2 | 5/2006 | Ohkubo et al. |
| 7,050,539 B2 | 5/2006 | Loef et al. |
| 7,054,411 B2 | 5/2006 | Katcha et al. |
| 7,072,439 B2 | 7/2006 | Radley et al. |
| 7,075,699 B2 | 7/2006 | Oldham et al. |
| 7,085,354 B2 | 8/2006 | Kanagami |
| 7,108,841 B2 | 9/2006 | Smalley et al. |
| 7,110,498 B2 | 9/2006 | Yamada |
| 7,130,380 B2 | 10/2006 | Lovoi et al. |
| 7,130,381 B2 | 10/2006 | Lovoi et al. |
| 7,203,283 B1 | 4/2007 | Puusaari |
| 7,206,381 B2 | 4/2007 | Shimono et al. |
| 7,215,741 B2 | 5/2007 | Ukita |
| 7,224,769 B2 | 5/2007 | Turner |
| 7,233,647 B2 | 6/2007 | Turner et al. |
| 7,236,568 B2 | 6/2007 | Dinsmore et al. |
| 7,286,642 B2 | 10/2007 | Ishikawa et al. |
| 7,305,065 B2 | 12/2007 | Takahashi et al. |
| 7,305,066 B2 | 12/2007 | Ukita |
| 7,317,784 B2 | 1/2008 | Durst et al. |
| 7,358,593 B2 | 4/2008 | Smith et al. |
| 7,382,862 B2 | 6/2008 | Bard et al. |
| 7,399,794 B2 | 7/2008 | Harmon et al. |
| 7,410,601 B2 | 8/2008 | Sato et al. |
| 7,428,298 B2 | 9/2008 | Bard et al. |
| 7,448,801 B2 | 11/2008 | Oettinger et al. |
| 7,448,802 B2 | 11/2008 | Oettinger et al. |
| 7,486,774 B2 | 2/2009 | Cain |
| 7,526,068 B2 | 4/2009 | Dinsmore |
| 7,529,345 B2 | 5/2009 | Bard et al. |
| 7,618,906 B2 | 11/2009 | Meilahti |
| 7,634,052 B2 | 12/2009 | Grodzins et al. |
| 7,649,980 B2 | 1/2010 | Aoki et al. |
| 7,650,050 B2 | 1/2010 | Haffner et al. |
| 7,657,002 B2 | 2/2010 | Burke et al. |
| 7,675,444 B1 | 3/2010 | Smith et al. |
| 7,680,652 B2 | 3/2010 | Giesbrecht et al. |
| 7,693,265 B2 | 4/2010 | Hauttmann et al. |
| 7,709,820 B2 | 5/2010 | Decker et al. |
| 7,737,424 B2 | 6/2010 | Xu et al. |
| 7,756,251 B2 | 7/2010 | Davis et al. |
| 7,826,586 B2 | 11/2010 | Nakayama et al. |
| 7,915,800 B2 | 3/2011 | Kim et al. |
| 7,983,394 B2 | 7/2011 | Kozaczek et al. |
| 8,242,704 B2 | 8/2012 | Lethellier |
| 8,331,533 B2 | 12/2012 | Yamamoto |
| 8,526,574 B2 | 9/2013 | Wang et al. |
| 8,581,437 B2 | 11/2013 | Delforge |
| 8,598,807 B2 | 12/2013 | Ji et al. |
| 8,761,344 B2 | 6/2014 | Reynolds et al. |
| 8,774,365 B2 | 7/2014 | Wang |
| 8,804,910 B1 | 8/2014 | Wang et al. |
| 2002/0075999 A1 | 6/2002 | Rother |
| 2002/0094064 A1 | 7/2002 | Zhou et al. |
| 2003/0096104 A1 | 5/2003 | Tobita et al. |
| 2003/0117770 A1 | 6/2003 | Montgomery et al. |
| 2003/0152700 A1 | 8/2003 | Asmussen et al. |
| 2003/0165418 A1 | 9/2003 | Ajayan et al. |
| 2004/0076260 A1 | 4/2004 | Charles, Jr. et al. |
| 2004/0131835 A1 | 7/2004 | Schmitt et al. |
| 2004/0192997 A1 | 9/2004 | Lovoi |
| 2005/0018817 A1 | 1/2005 | Oettinger et al. |
| 2005/0141669 A1 | 6/2005 | Shimono et al. |
| 2005/0207537 A1 | 9/2005 | Ukita |
| 2006/0073682 A1 | 4/2006 | Furukawa et al. |
| 2006/0098778 A1 | 5/2006 | Oettinger et al. |
| 2006/0210020 A1 | 9/2006 | Takahashi et al. |
| 2006/0233307 A1 | 10/2006 | Dinsmore |
| 2006/0269048 A1 | 11/2006 | Cain |
| 2006/0280289 A1 | 12/2006 | Hanington et al. |
| 2007/0025516 A1 | 2/2007 | Bard et al. |
| 2007/0111617 A1 | 5/2007 | Meilahti |
| 2007/0133921 A1 | 6/2007 | Haffner et al. |
| 2007/0165780 A1 | 7/2007 | Durst et al. |
| 2007/0172104 A1 | 7/2007 | Nishide et al. |
| 2007/0183576 A1 | 8/2007 | Burke et al. |
| 2007/0217574 A1 | 9/2007 | Beyerlein |
| 2008/0199399 A1 | 8/2008 | Chen et al. |
| 2008/0296479 A1 | 12/2008 | Anderson et al. |
| 2008/0296518 A1 | 12/2008 | Xu et al. |
| 2008/0317982 A1 | 12/2008 | Hecht et al. |
| 2009/0085426 A1 | 4/2009 | Davis et al. |
| 2009/0086923 A1 | 4/2009 | Davis et al. |
| 2009/0213914 A1 | 8/2009 | Dong et al. |
| 2009/0243028 A1 | 10/2009 | Dong et al. |
| 2010/0098216 A1 | 4/2010 | Dobson |
| 2010/0126660 A1 | 5/2010 | O'Hara |
| 2010/0140497 A1 | 6/2010 | Damiano, Jr. et al. |
| 2010/0189225 A1 | 7/2010 | Ernest et al. |
| 2010/0239828 A1 | 9/2010 | Cornaby et al. |
| 2010/0243895 A1 | 9/2010 | Xu et al. |
| 2010/0285271 A1 | 11/2010 | Davis et al. |
| 2011/0022446 A1 | 1/2011 | Carney, II et al. |
| 2011/0121179 A1 | 5/2011 | Liddiard et al. |
| 2012/0025110 A1 | 2/2012 | Davis et al. |
| 2012/0076276 A1 | 3/2012 | Wang et al. |
| 2012/0087476 A1 | 4/2012 | Liddiard et al. |
| 2014/0029719 A1* | 1/2014 | Lee .................. A61B 6/145 378/38 |

FOREIGN PATENT DOCUMENTS

| | | |
|---|---|---|
| DE | 19818057 | 11/1999 |
| EP | 0297808 | 1/1989 |
| EP | 0330456 | 8/1989 |
| EP | 0400655 | 5/1990 |
| EP | 0676772 | 3/1995 |
| GB | 1252290 | 11/1971 |
| JP | 57 082954 | 5/1982 |
| JP | 3170673 | 7/1991 |
| JP | 4171700 | 6/1992 |
| JP | 5066300 | 3/1993 |
| JP | 5135722 | 6/1993 |
| JP | 06119893 | 4/1994 |
| JP | 6289145 | 10/1994 |
| JP | 6343478 | 12/1994 |
| JP | 8315783 | 11/1996 |
| JP | 2003/007237 | 1/2003 |
| JP | 2003/088383 | 3/2003 |
| JP | 2003/510236 | 3/2003 |
| JP | 2003/211396 | 7/2003 |
| JP | 2006/297549 | 11/2006 |
| KR | 10-2005-0107094 | 11/2005 |
| KR | 10-1147059 | 5/2012 |
| WO | WO 99/65821 | 12/1999 |
| WO | WO 00/09443 | 2/2000 |
| WO | WO 00/17102 | 3/2000 |
| WO | WO 03/076951 | 9/2003 |
| WO | WO 2008/052002 | 5/2008 |

(56) References Cited

FOREIGN PATENT DOCUMENTS

| WO | WO 2009/009610 | 1/2009 |
|---|---|---|
| WO | WO 2009/045915 | 4/2009 |
| WO | WO 2009/085351 | 7/2009 |
| WO | WO 2010/107600 | 9/2010 |
| WO | WO 2012/039823 | 3/2012 |

OTHER PUBLICATIONS

Blanquart et al.; "XPAD, a New Read-out Pixel Chip for X-ray Counting"; IEEE Xplore; Mar. 25, 2009.

Chakrapani et al.; Capillarity-Driven Assembly of Two-Dimensional Cellular Carbon Nanotube Foams; PNAS; Mar. 23, 2004; pp. 4009-4012; vol. 101; No. 12.

Chen et al.; "Carbon-nanotube metal-matrix composites prepared by electroless plating," Composites Science and Technology, 2000, pp. 301-306, vol. 60.

Coleman et al.; "Mechanical Reinforcement of Polymers Using Carbon Nanotubes"; Adv. Mater. 2006, 18, 689-706.

Coleman et al.; "Small but strong: A review of the mechanical properties of carbon nanotube-polymer composites"; Carbon 44 (2006) 1624-1652.

Comfort; "Plasma-enhanced chemical vapor deposition of in situ doped epitaxial silicon at low temperatures," J. Appl. Phys. 65, 1067 (1989).

Das et al.; "Chemical vapor deposition of boron on a beryllium surface," Thin Solid Films, 83(1), pp. 53-60, (1981).

Das et al.; "Tribological behavior of improved chemically vapor-deposited boron on beryllium," Thin Solid Films, 108(2), 181-188, (1983).

Flahaut et al.; "Carbon Nanotube-metal-oxide nanocomposites; microstructure, electrical conductivity and mechanical properties," Acta mater., 2000, pp. 3803-3812.Vo. 48.

Gevin et al.; "IDeF-X V1.0: performances of a new CMOS multichannel analogue readout ASIC for Cd(Zn)Te detectors", IDDD, Oct. 2005, 433-437, vol. 1.

Grybos et al., "DEDIX—development of fully integrated multichannel ASCI for high count rate digital x-ray imaging systems", IEEE, 693-696, vol. 2. (2006).

Grybos et al., "Measurements of matching and high count rate performance of multichannel ASIC for digital x-ray imaging systems", IEEE, Aug. 2007, 1207-1215, vol. 54, Issue 4.

Grybos et al., "Pole-Zero cancellation circuit with pulse pile-up tracking system for low noise charge-sensitive amplifiers", Feb. 2008, 583-590, vol. 55, Issue 1.

Hanigofsky et al.; "Composition and microstructure of chemically vapor-deposited boron nitride, aluminum nitride, and boron nitride + aluminum nitride composites," J. Amer. Ceramic Soc. 74, 301 (1991).

Hexcel Corporation; "Prepreg Technology" brochure; (2005) http://www.hexcel.com/Reso2882urces/DataSheets/Brochure-Data-Sheets/Prepreg_Technology.pdf.

http://www.orau.org/ptp/collectio/xraytubescollidge/MachlettCW250T.htm, 1999, 2 pages.

Hu et al.; "Carbon Nanotube Thin Films: Fabrication, Properties, and Applications"; 2010 American Chemical Society Jul. 22, 2010.

Hutchison; "Vertically aligned carbon nanotubes as a framework for microfabrication of high aspect ratio mems," 2008, pp. 1-50.

Jiang et al., "Carbon nanotubes-metal nitride composites; a new class of nanocomposites with enhanced electrical properties," J. Mater. Chem., 2005, pp. 260-266, vol. 15.

Komatsu et al.; "Influence of atomic hydrogen on the growth reactions of amorphous boron films in a low-pressure $B_2H_6 + He + H_2$ plasma", J. Appl. Phys. 64, 1878 (1988).

Komatsu et al.; "Transition from amorphous to crystal growth of boron films in plasma-enhanced chemical vapor deposition with $B_2H_6$ +He," J. Appl. Phys., 66, 466 (1989).

Komatsu et al.; "Transition from thermal-to electron-impact decomposition of diborane in plasma-enhanced chemical vapor deposition of boron films from $B_2H_6$ +He," J. Appl. Phys. 66, 1180 (1989).

Lee et al.; "Kinetic analysis of chemical vapor deposition of boron nitride," J. Amer. Ceramic Soc. 74, 2642 (1991).

Li et al., "Bottom-up approach for carbon nanotube interconnects," Applied Physics Letters, Apr. 14, 2003, pp. 2491-2493, vol. 82 No. 15.

Ma et al.; "Processing and properties of carbon nanotubes-nano-SIC ceramic", Journal of Materials Science 1998, pp. 5243-5246, vol. 33.

Maya et al.; "Pyrolytic deposition of carbon films containing nitrogen and/or boron," J. Amer. Ceramic Soc. 73, 1912 (1990).

Michaelidis et al.; "Analysis of chemical vapor deposition of boron," J. Electrochem. Soc. 132, 1757 (1985).

Micro X-ray Tube Operation Manual, X-ray and Specialty Instruments Inc., 1996, 5 pages.

Moore et al.; "Properties and characterization of codeposited boron nitride and carbon materials," J. Appl. Phys. 65, 5109 (1989).

Najafi et al.; "Radiation resistant polymer-carbon nanotube nanocomposite thin films"; Department of Materials Science and Engineering . . . Nov. 21, 2004.

Nakajima et al; Trial Use of Carbon-Fiber-Reinforced Plastic as a Non-Bragg Window Material of X-Ray Transmission; Rev. Sci. Instrum.; Jul. 1989; pp. 2432-2435; vol. 60, No. 7.

Nakamura; "Preparation and properties of amorphous boron nitride films by molecular flow chemical vapor deposition," J. Electrochem. Soc. 132, 1757 (1985).

Panayiotatos et al.; "Mechanical performance and growth characteristics of boron nitride films with respect to their optical, compositional properties and density," Surface and Coatings Technology, 151-152 (2002) 155-159.

PCT Application No. PCT/US2011/044168; Filed Mar. 28, 2012; Kang Hyun Il; International Search Report mailed Mar. 28, 2012.

Peigney et al.; "Carbon nanotubes in novel ceramic matrix nanocomposites," Ceramics International, 2000, pp. 677-683, vol. 26.

Perkins et al.; "Synchrotronradiation deposition of boron and boron carbide films from boranes and carboranes: decaborane," J. Appl. Phys. 69,4103 (1991).

Powell et al.; "Metalized polyimide filters for x-ray astronomy and other applications," SPIE, pp. 432-440, vol. 3113; (Jul. 1997).

Rankov et al.; "A novel correlated double sampling poly-Si circuit for readout systems in large area x-ray sensors", IEEE, May 2005, 728-731, vol. 1.

Roca I Cabarrocas et al.; "In situ study of the thermal decomposition of $B_2H_6$ by combining spectroscopic ellipsometry and Kelvin probe measurements," J. Appl. Phys. 66, 3286 (1989).

Satishkumar et al.; "Synthesis of metal oxide nanorods using carbon nanotubes as templates," Journal of Materials Chemistry, 2000, pp. 2115-2119, vol. 10.

Scholze et al.; "Detection efficiency of energy-dispersive detectors with low-energy windows" X-Ray Spectrometry, X-Ray Spectrom, 2005: 34: 473-476.

Sheather; "The support of thin windows for x-ray proportional counters," Journal Phys,E., Apr. 1973, pp. 319-322, vol. 6, No. 4.

Shirai et al.; "Characterization of hydrogenated amorphous boron films prepared by electron cyclotron resonance plasma chemical vapor deposition method," J. Appl. Phys. 67, 6286 (1990).

Tamura et al "Development of ASICs for CdTe Pixel and Line Sensors", IEEE Transactions on Nuclear Science, vol. 52, No, 5, Oct. 2005.

Tien-Hui Lin et al., "An investigation on the films used as the windows of ultra-soft X-ray counters." Acta Physica Sinica, vol. 27, No. 3, pp. 276-283, May 1978, abstract only.

U.S. Appl. No. 12/890,325, filed Sep. 24, 2010; Dongbing Wang; Notice of Allowance dated Jul. 16, 2013.

U.S. Appl. No. 12/890,325, filed Sep. 24, 2010; Dongbing Wang; Office Action dated Sep. 7, 2012.

U.S. Appl. No. 12/899,750, filed Oct. 7, 2010; Steven Liddiard; Notice of Allowance dated Jun. 4, 2013.

U.S. Appl. No. 12/352,864, filed Jan. 13, 2010; Michael Lines.

U.S. Appl. No. 12/726,120, filed Mar. 17, 2010; Michael Lines.

Vajtai et al.; Building Carbon Nanotubes and Their Smart Architectures; Smart Mater. Struct.; 2002; vol. 11; pp. 691-698.

(56) References Cited

OTHER PUBLICATIONS

Vandenbulcke; "Theoretical and experimental studies on the chemical vapor deposition of boron carbide," Indust. Eng. Chem. Prod. Res. Dev. 24, 568 (1985).

Viitanen et al., Comparison of Ultrathin X-Ray Window Designs, presented at the Soft X-rays in the 21st Century Conference held in Provo, Utah Feb. 10-13, 1993, pp. 182-190.

Wagner et al, "Effects of Scatter in Dual-Energy Imaging: An Alternative Analysis"; IEEE; Sep. 1989, vol. 8. No. 3.

Wang et al.; "Highly oriented carbon nanotube papers made of aligned carbon nanotubes"; Tsinghua-Foxconn Nanotechnology Research Center and Department of Physics; Published Jan. 31, 2008.

Winter et al.; "Diborane-free boronization," Fusion Technol. 20, 225 (1991).

Wu et al.; "Mechanical properties and thermo-gravimetric analysis of PBO thin films"; Advanced Materials Laboratory, Institute of Electro-Optical Engineering; Apr. 30, 2006.

www.moxtek,com, Moxtek, Sealed Proportional Counter X-Ray Windows, Oct. 2007, 3 pages.

www.moxtek.com, Moxtek, AP3 Windows, Ultra-thin Polymer X-Ray Windows, Sep. 2006, 2 pages.

www.moxtek.com, Moxtek, DuraBeryllium X-Ray Windows, May 2007, 2 pages.

www.moxtek.com, Moxtek, ProLine Series 10 Windows, Ultra-thin Polymer X-Ray Windows, Sep. 2006, 2 pages.

www.moxtek.com, X-Ray Windows, ProLINE Series 20 Windows Ultra-thin Polymer X-ray Windows, 2 pages. Applicant believes that this product was offered for sale prior to the filing date of applicant's application. (2006).

Xie et al.; "Dispersion and alignment of carbon nanotubes in polymer matrix: A review"; Center for Advanced Materials Technology; Apr. 20, 2005.

Yan et al.; Fabrications of Three-Dimensional ZnO—Carbon Nanotube (CNT) Hybrids Using Self-Assembled CNT Micropatterns as Framework, 2007. pp. 17254-17259, vol. III.

Zhang et al.; "Superaligned Carbon Nanotube Grid for High Resolution Transmission Electron Microscopy of Nanomaterials"; 2008 American Chemical Society.

\* cited by examiner

X-RAY TUBE AND RECEIVER INSIDE MOUTH

CLAIM OF PRIORITY

This claims priority to U.S. Provisional Patent Application No. 61/814,144, filed on Apr. 19, 2013, which is hereby incorporated herein by reference in its entirety.

FIELD OF THE INVENTION

The present application is related generally to dental x-rays.

BACKGROUND

Typical dental x-rays are performed with an x-ray source or an x-ray receiver disposed outside the mouth of a patient, and the other of the x-ray source or x-ray receiver disposed inside the mouth of the patient. The patient's cheek or lip may force a gap between source or receiver and the tooth. Because of this gap, increased x-ray flux may be needed to obtain an image of the tooth. The cheek or lip may also block the medical professional's view, resulting in images taken at incorrect locations. As a result, the x-ray image may need to be retaken. Increased x-ray flux due to the large gap and due to retakes of the image may expose the patient to extra, undesirable radiation, which can cause health problems. For example, see Korean Patent Number KR 10-1147059 and U.S. Pat. Nos. 3,752,990, 3,906,235, 4,100,417, 4,193,002.

SUMMARY

It has been recognized that it would be advantageous to reduce patient exposure to radiation while taking dental x-rays. The present invention is directed to a method and a device that satisfies these needs.

The device for dental x-rays can comprise an x-ray source sized and configured to have at least an x-ray emission portion of the x-ray source disposed in a patient's mouth and an x-ray receiver sized and configured to have at least an x-ray image receiving portion of the x-ray receiver disposed in the patient's mouth. A bite holder can be attached to the x-ray source and to the x-ray receiver such that an x-ray emission window of the x-ray source faces the x-ray image receiving portion of the x-ray receiver. There can be a gap created by the bite holder between the x-ray source and the x-ray receiver. The gap can be sized and configured to extend across a tooth in the patient's mouth and to hold the x-ray source on one side of the tooth and the x-ray receiver on an opposite side of the patient's tooth.

The method, of taking x-rays of a patient's tooth, can comprise:
1. placing an x-ray emission portion of an x-ray source on one side of the tooth inside of a mouth of the patient and an x-ray image receiving portion of an x-ray receiver on an opposite side of the tooth inside the mouth, wherein:
   a. the source or the receiver is between a cheek or lip of the mouth and the tooth; and
   b. the other of the source or the receiver is on an opposite side of the tooth; and
2. emitting x-rays from the source through the tooth and onto the receiver.

Figure 2:
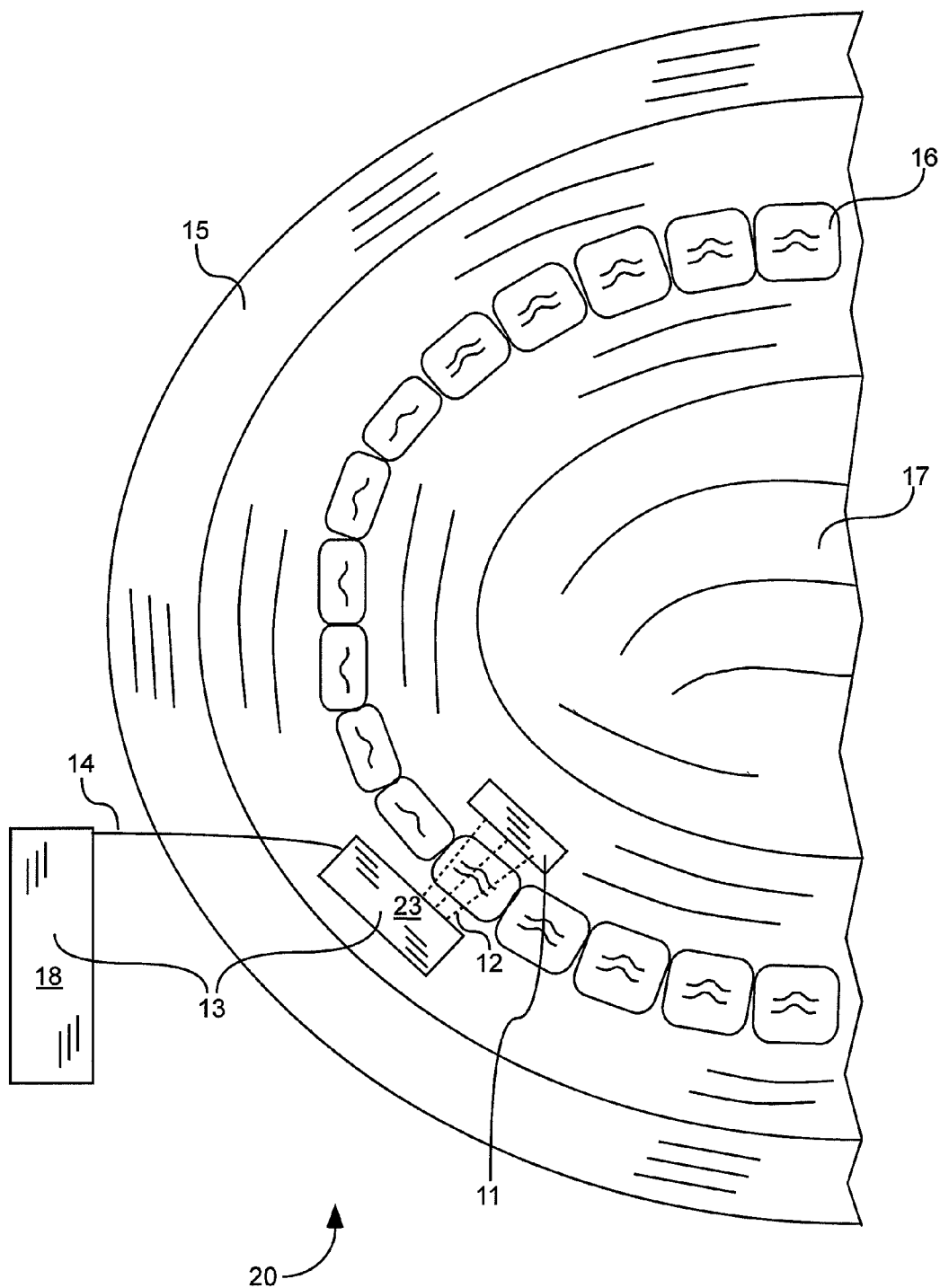
FIG. 2 is a schematic view of a dental x-ray device 20, or method of taking dental x-rays, including at least a portion of a receiver 11 disposed between a tongue 17 and a tooth 16 of the patient, and at least a portion of a x-ray source 13 disposed between a cheek or lip 15 and a tooth 16 of the patient, in accordance with an embodiment of the present invention.
Figure 5:
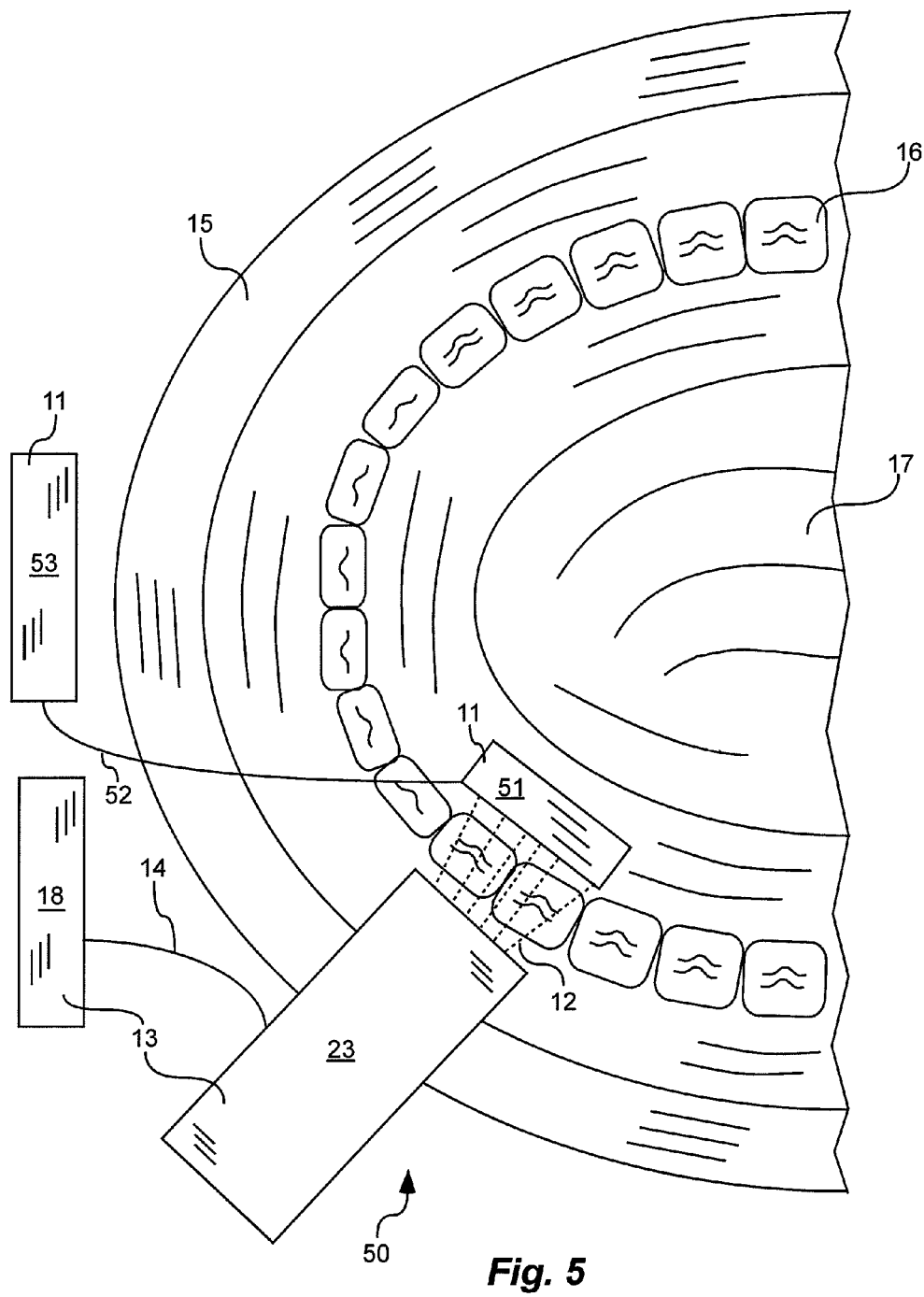
FIG. 5 is a schematic view of a dental x-ray device 50, or method of taking dental x-rays, for taking dental x-rays of multiple teeth 16 at one time, in accordance with an embodiment of the present invention.
Figure 7:
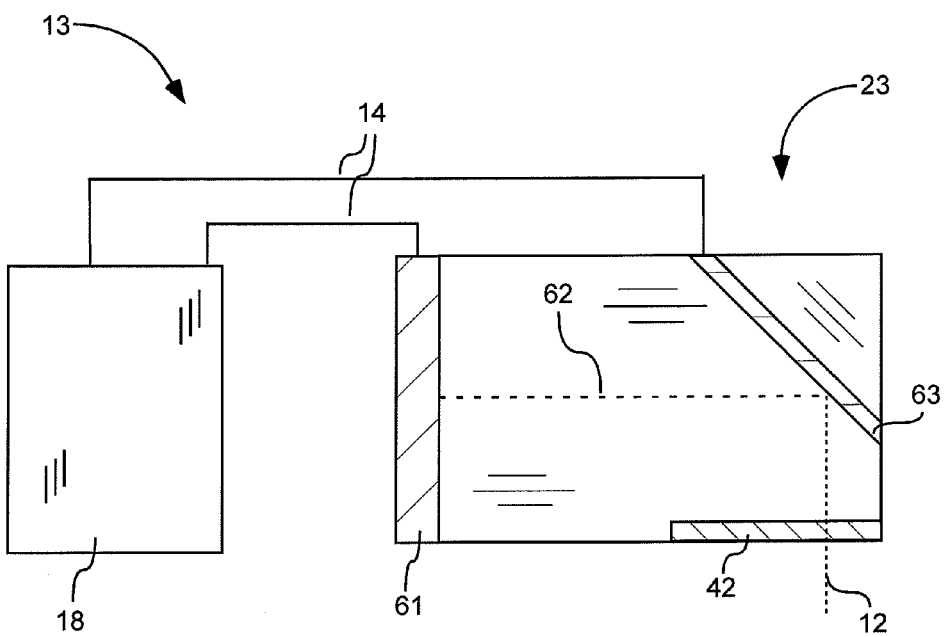

Alternatively, the power supply 18 can be as shown in FIGS. 2, 5 and 7.

Figure 8:
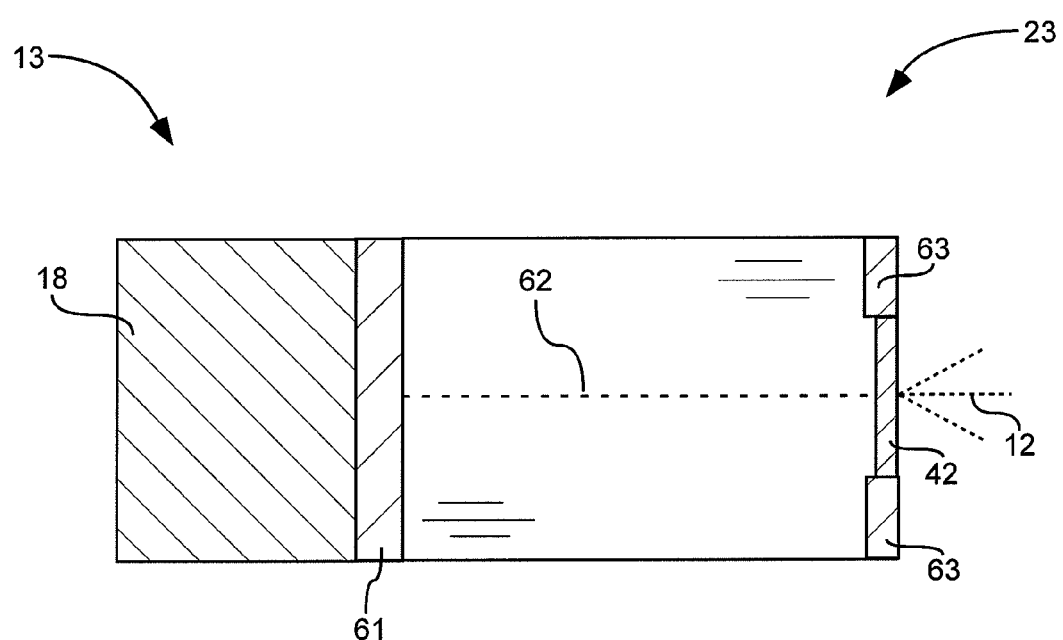
Figure 9:
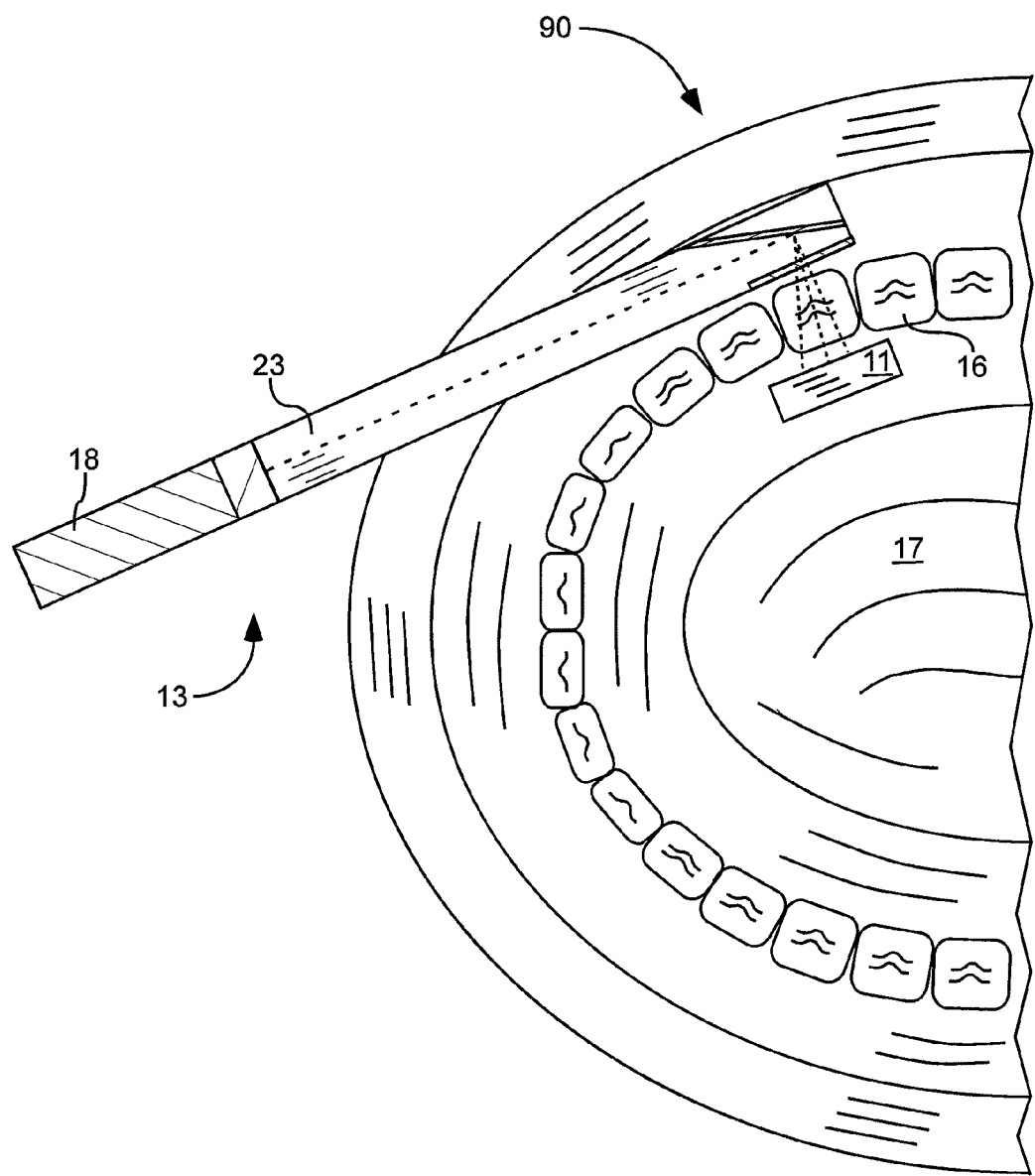

FIG. 7 is a schematic cross-sectional side view of a dental, side-window x-ray tube 23 connected to a power supply 18 by a flexible cable 14, in accordance with an embodiment of the present invention;

FIG. 8 is a schematic cross-sectional side view of a transmission or end window, dental x-ray tube 23, in accordance with an embodiment of the present invention; and FIG. 9 is a schematic view of a dental x-ray device 90, or method of taking dental x-rays, in accordance with an embodiment of the present invention.

DEFINITIONS

As used herein, the term "tooth" includes a single tooth or multiple teeth. The term "tooth" includes not only the tooth itself but also surrounding periodontal tissues and alveolar bone.

DETAILED DESCRIPTION

As illustrated in FIGS. 1-5 and 9, x-ray devices 10, 20, 30, 40, 50, and 90 for dental x-rays are shown comprising an x-ray source 13 and an x-ray receiver 11. The source 13 and the receiver 11 can be sized and configured to be disposed at least partially in a patient's mouth. Configured to be disposed in a patient's mouth means that these units 11 and 13 are shaped and made of materials that will fit properly in the patient's mouth, are designed for patient comfort, and will result in optimal safety for the patient.

Figure 1:
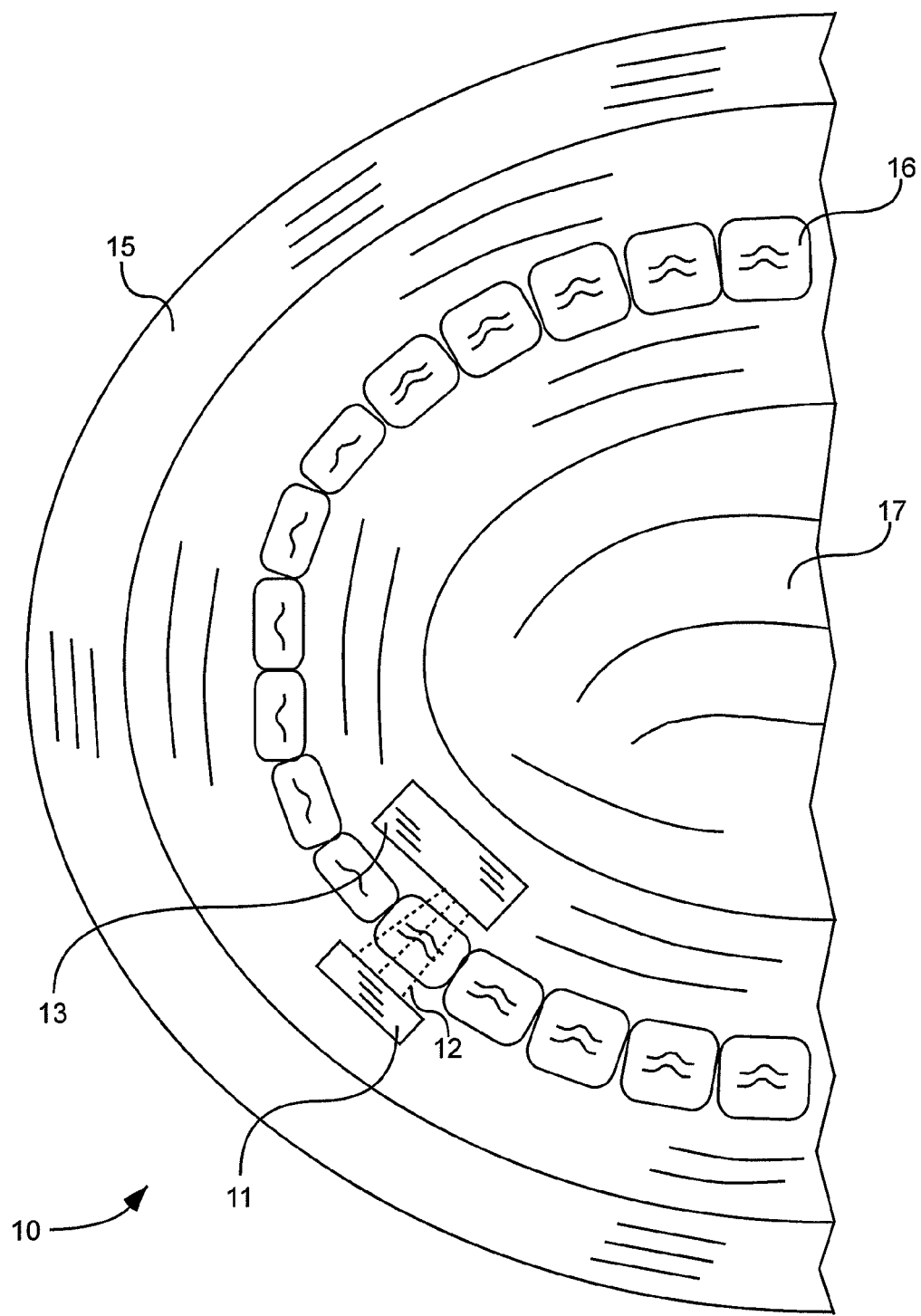
FIG. 1 is a schematic view of a dental x-ray device 10, or method of taking dental x-rays, including at least a portion of an x-ray source 13 disposed between a tongue 17 and a tooth 16 of the patient and at least a portion of a receiver 11 disposed between a cheek or lip 15 and a tooth 16 of the patient, in accordance with an embodiment of the present invention.

As shown on x-ray device 10 of FIG. 1, at least a portion of the source 13 can be disposed between a tongue 17 of a patient and a tooth 16. At least a portion of the receiver 11 can be disposed between a cheek or lip 15 of the patient and the tooth 16.

As shown on x-ray device 20 of FIG. 2, at least a portion of the receiver 11 can be disposed between a tongue 17 of a patient and a tooth 16. At least a portion of the source 13 can be disposed between a cheek or lip 15 of the patient and the tooth 16.

X-rays 12 can be emitted from the source 13 through the tooth 16 to the receiver 11. The relative position of the source 13 and the receiver 11 may depend on manufacturability considerations of these devices, patient comfort, and space in the patient's mouth.

Figure 6:
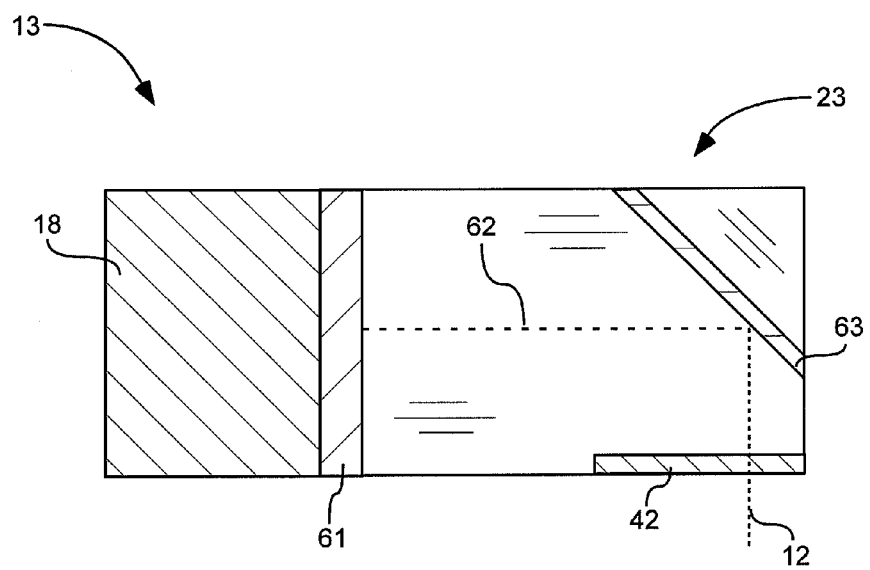
FIG. 6 is a schematic cross-sectional side view of a dental, side-window x-ray tube 23 firmly mounted to a battery power supply 18, in accordance with an embodiment of the present invention.

As shown in FIGS. 2 and 5-9, the source 13 can include a power supply 18 and an x-ray tube 23. The power supply 18 can be firmly mounted to the x-ray tube 23 as shown in FIGS. 6, 8, and 9. Alternatively, the power supply 18 can be connected to the x-ray tube 23 by a flexible cable 14 as shown in FIGS. 2, 5 and 7.

The entire x-ray tube 23, or only a portion of the x-ray tube, can be disposed inside the mouth of the patient. The portion of the x-ray source 13 inside the mouth of the patient can include an x-ray emission portion of the x-ray source 13. For example, an x-ray window 42 of the x-ray tube 23 (see FIGS. 6-8) or optics attached to an end of the x-ray tube (not shown in the figures) can be disposed inside the mouth. An x-ray tube anode 63 can also be disposed inside the mouth. The cathode 61 can be disposed outside of the mouth. The power supply 18 can be disposed outside of the mouth.

The receiver 11 can be a photographic film configured to record an image of x-ray exposure on the film. The receiver 11 can be an electronic x-ray sensor or detector electrically connected to an external device for creating an image of the tooth 16.

All or a portion of the receiver 11 can be disposed inside the mouth of the patient. The portion of the x-ray receiver 11 inside the mouth of the patient can include an x-ray image receiving portion 51 (see FIG. 5). The x-ray image receiving portion 51 can be an electronic sensor or detector which can be disposed partially or entirely in the mouth. The x-ray image receiving portion 51 can be electrically connected (e.g. see cable 52 in FIG. 5) to associated electronic equipment 53 which can be disposed outside of the mouth.

The source 13 can be configured to direct x-rays 12 primarily at the tooth 16 and to block x-rays 12 from being emitted in other directions, such as with appropriately placed shielding. A side window x-ray tube can naturally provide some of this shielding.

By disposing both the source 13 and the receiver 11 units at least partially in the mouth of the patient while doing the dental x-ray, multiple advantages can be realized. First, by disposing these units 11 and 13 adjacent to the tooth 16, it is easier to irradiate the correct area, thus reducing retakes of the x-ray image. Second, by disposing these units 11 and 13 adjacent to the tooth 16, less radiation is required to obtain a desired image than would otherwise be the case if one of these devices 11 or 13 was disposed outside the mouth. Reduced radiation can result in reduced health problems caused by x-ray radiation. Third, due to reduced required radiation, the source 13 can be powered by a portable power supply 18.

Reduced patient radiation exposure can be quantified by an amount of electrical current 62 between a cathode 61 and an anode 63 of the source 13 for recording an image of the tooth 16 (anode and cathode are shown in FIGS. 6-8). For example, the electrical current 62 to record a single image of a tooth 16 can be less than 0.1 milliamps in one embodiment, less than 1 milliamp in another embodiment, less than 3 milliamps in another embodiment, or between 0.01 and 1 milliamp in another embodiment.

Reduced patient radiation exposure can be quantified by patient radiation exposure in micro sieverts ($\mu Sv$). This exposure can result from taking an image of a single tooth 16. For example, patient radiation exposure to record a single image of a tooth can be less than 2 micro sieverts ($\mu Sv$) in one embodiment, less than 1 $\mu Sv$ in another embodiment, less than 0.3 $\mu Sv$ in another embodiment, or less than 0.15 $\mu Sv$ in another embodiment. This exposure can result from recording a full mouth series of x-rays of all of the patient's teeth and adjacent hard tissue (FMX). For example, patient radiation exposure for FMX can be less than 15 micro sieverts ($\mu Sv$), less than 5 $\mu Sv$, or less than 2.5 $\mu Sv$.

Figure 3:
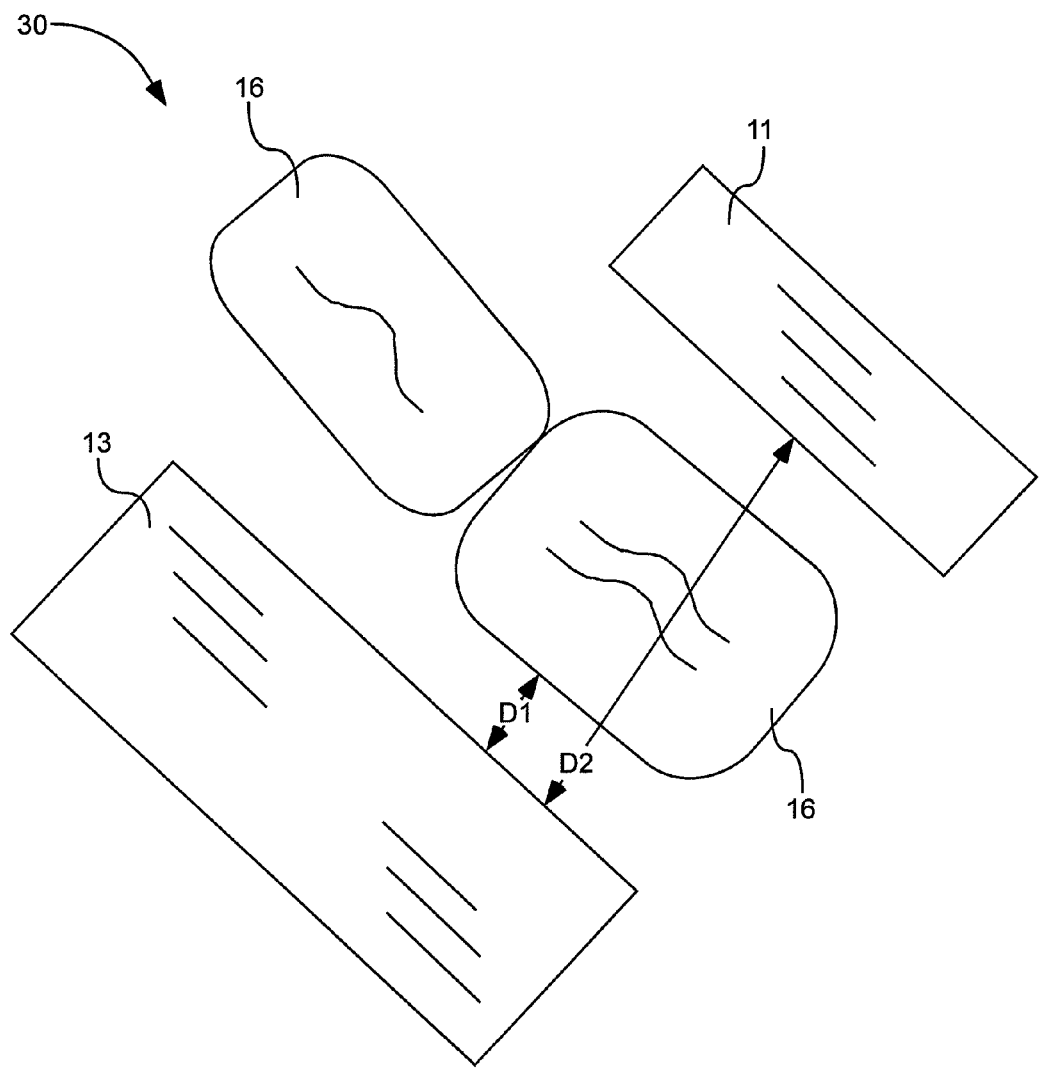
FIG. 3 is a schematic view of a dental x-ray device 30, or method of taking dental x-rays, including at least a portion of a receiver 11 and at least a portion of an x-ray source 13 disposed inside a mouth of a patient and showing a distance D1 between a tooth 16 and the x-ray source 13 and a distance D2 between the receiver 11 and the x-ray source 13, in accordance with an embodiment of the present invention.

Shown in FIG. 3 is x-ray device 30, which is an expanded view of x-ray devices 10 or 20, in order to show a more detailed view. A distance D1 between the source 13 and the tooth 16, and a distance D2 between the source 13 and the receiver 11, can be small in order to help ensure the image is taken in the correct location and to minimize patient radiation exposure in taking the image. For example, the distance D1 between the source 13 and the tooth 16 can be less than 5 mm in one embodiment, less than 10 mm in another embodiment, less than 15 mm in another embodiment, between 1 mm and 5 mm in another embodiment, or between 1 mm and 15 mm in another embodiment. As another example, the distance D2 between the source 13 and the receiver 11 can be less than less than 20 mm in one embodiment, less than 40 mm in another embodiment, or between 10 mm and 40 mm in another embodiment. In one embodiment, the distance D2 between the source 13 and the receiver 11 may be at a minimum when the distance D2 is approximately the width of the tooth 16 and may be at a maximum when the source 13 and the receiver 11 are pressed against a cheek or lip and/or against a tongue, respectively.

Figure 4:
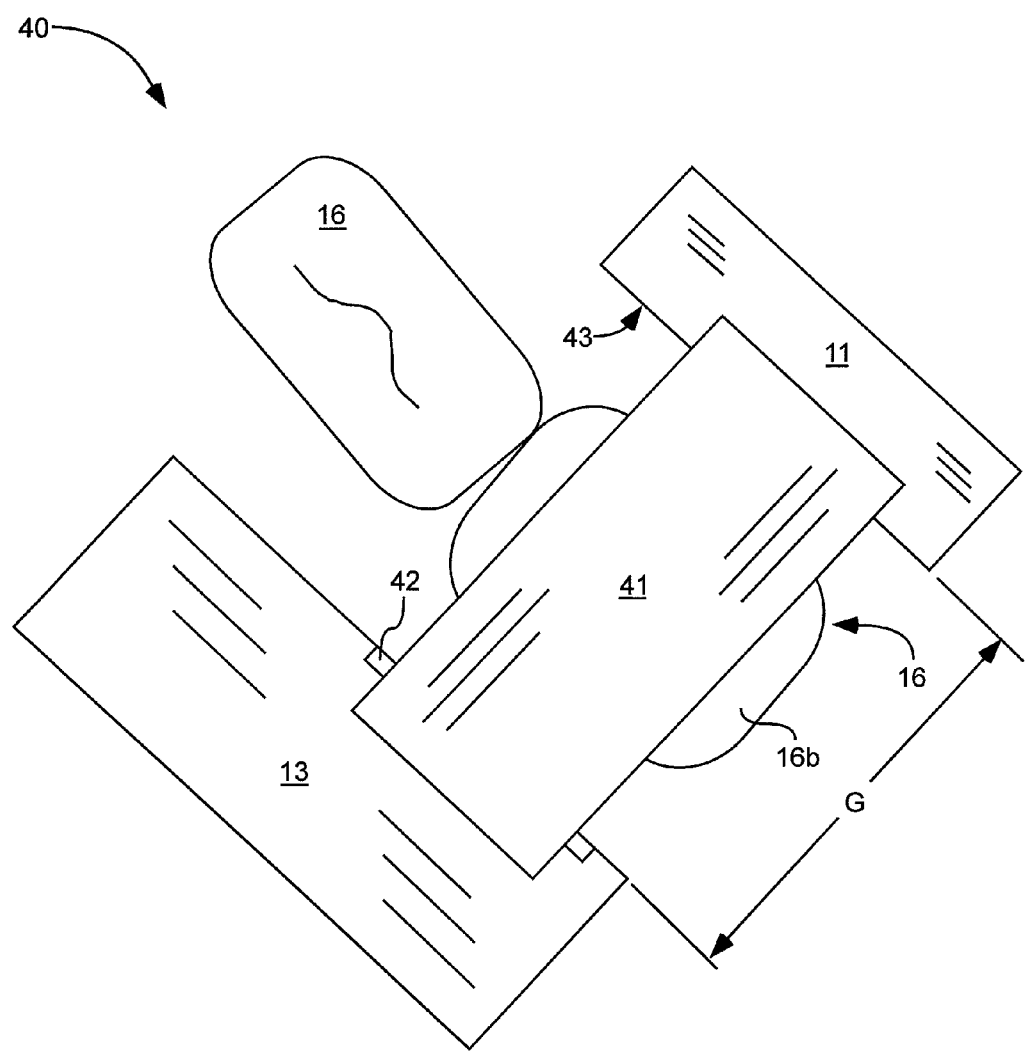
FIG. 4 is a schematic view of a dental x-ray device 40, or method of taking dental x-rays, including at least a portion of a receiver 11 and at least a portion of an x-ray source 13 disposed inside a mouth of a patient with a bite holder 41 extending across a biting surface 16b of the tooth 16 and holding the source 13 in position on one side of the tooth 16 and the receiver 11 in position on an opposite side of the tooth 16, in accordance with an embodiment of the present invention.

As shown on x-ray device 40 in FIG. 4, a bite holder 41 can be attached to the source 13 and to the receiver 11. The bite holder 41 can extend across a biting surface 16b of the tooth 16 and can hold the source 13 in position on one side of the tooth 16 and the receiver 11 in position on an opposite side of the tooth 16.

An x-ray emission window 42 of the source 13 can face a portion 43 of the receiver 11 configured to receive the x-rays 12. A gap G on the bite holder 41 between the source 13 and the receiver 11 can be sized and configured to extend across a tooth in the patient's mouth to hold the source 13 on one side of the tooth 16 and the receiver 11 on an opposite side of the patient's tooth 16. The bite holder 41 can be configured to hold the source 13 between the tooth 16 and the cheek or lip 15 and to hold the receiver 11 on an opposite side of the tooth 16 between the tongue 17 and the tooth 16. The bite holder 41 can be configured to hold the receiver 11 between the tooth 16 and the cheek or lip 15 and to hold the source 13 on an opposite side of the tooth 16 between the tongue 17 and the tooth 16. Alternatively, the bite holder 41 can be configured for either position, that is to hold either the receiver 11 or the source 13 between the tooth 16 and the cheek or lip 15 and to hold the other of the receiver 11 or the source 13 on an opposite side of the tooth 16 between the tongue 17 and the tooth 16. The gap can be sized and configured to extend across an adult human's tooth, a human child's tooth, or the tooth of an animal. In one example, the gap may be adjustable by adjusting a position of the receiver 11 or the source 13 on the bite holder 41 to accommodate teeth 16 or mouths of different sizes. The bite holder 41 may hold the source 13 and the receiver 11 in position about the tooth 16 when the patient "bites" the bite holder, or applies a pressure to the bite holder 41 using a tooth opposite the tooth 16 receiving the x-rays 12.

As shown on x-ray device 50 in FIG. 5, the term "tooth" 16 as mentioned herein can include multiple teeth and the device can be configured to emit x-rays 12 through and to record an image of multiple teeth at one time. Alternatively, as shown in FIGS. 1-2, the device can be configured to emit x-rays 12 through and to record an image of a single tooth 16 at one time. Although FIG. 5 illustrates images of two teeth being recorded at one time, the x-ray device 50 may be configured to record images more than two teeth at one time.

As shown on x-ray sources 13 in FIGS. 6-7 and 9, the x-ray tube 23 can be or can include a side window x-ray tube. Electrons in an electrical current 62 can be emitted from a cathode 61 and can strike an anode 63. The anode 63 can include a target material configured to produce x-rays 12 in response to impinging electrons. The anode can at least partially face a window 42 and can emit x-rays 12 through an interior of the x-ray tube 23 and out through the window 42.

As shown on x-ray sources 13 FIGS. 5 and 8, the x-ray tube 23 can be a transmission or end window type. Electrons in an electrical current 62 can be emitted from a cathode 61 and can strike a window 42 portion of the anode 63. The window 42 can include a target material configured to produce x-rays 12 in response to impinging electrons. Manufacturability, patient comfort, and whether the teeth 16 examined are at a front or back of the mouth may be considered in deciding between a side window or end window x-ray source.

As shown in FIGS. 6, 8, and 9 the x-ray source 13 can include an x-ray tube 23 with a battery-operated power supply 18 firmly mounted at one end of the tube 23 (e.g. the cathode 61 end). Alternatively, as shown in FIG. 7, the x-ray source 13 can include an x-ray tube 23 powered by a power supply 18 that is attached to the x-ray tube 23 only by a flexible cable 14 (not firmly mounted to the x-ray tube 23). The power supply 18 can be electrical power from a wall outlet or can be a battery and can transmit electrical power through an electrical cable 14. Thus, the source 13 can be a battery-powered, portable power supply 18.

Because of the proximity of the source 13 to the tooth 16, the power of the x-ray tube and the voltage between the cathode 61 and the anode 63 can be relatively small. For example, the power supply 18 can be configured to provide a bias voltage between the anode 63 and the cathode 61 of less than 51 kilovolts in one embodiment.

Method

A method of taking x-rays of a patient's tooth can comprise:

1. placing an x-ray emission portion of a source 13 on one side of the tooth 16 inside of a mouth of the patient and an x-ray image receiving portion of an x-ray receiver 11 on an opposite side of the tooth 16 inside the mouth, wherein:
    a. the source 13 or the receiver 11 is between a cheek or lip 15 of the mouth and the tooth 16; and
    b. the other of the source 13 or the receiver 11 is on an opposite side of the tooth 16; and
2. emitting x-rays 12 from the source 13 through the tooth 16 and onto the receiver 11.

The source 13 in the method can include an x-ray tube 23 and an electrical power supply 18. The power supply can be attached to the x-ray tube 23 only by a flexible cable 14 or can be firmly mounted to the x-ray tube 23.

The source 13 in the method can be between the tooth 16 and the cheek or lip 15 and the receiver 11 can be on an opposite side of the tooth 16 between a tongue 17 of the mouth and the tooth 16. The receiver 11 in the method can be between the tooth 16 and the cheek or lip 15 and the source 13 can be on an opposite side of the tooth 16 between a tongue 17 of the mouth and the tooth 16.

The receiver 11 in the method can be a photographic film configured to record an image of x-ray exposure on the film. The receiver 11 in the method can be an electronic x-ray sensor or detector electrically connected to an external device for creating an image of the tooth 16.

The tooth 16 in the method can include multiple teeth and the receiver 11 can record an image of multiple teeth at one time. The tooth 16 in the method can include a single tooth 16 and the receiver 11 can record an image of a single tooth 16 at one time.

The source 13 in the method can be a side window or transmission end window x-ray tube 23. The source 13 in the method can be configured to direct x-rays 12 primarily at the tooth 16 and to block x-rays 12 from being emitted in other directions. A voltage between an anode and a cathode of the source 13 can be less than 51 kilovolts.

A distance in the method between the source 13 and the tooth 16 can be less than 5 mm. A distance between the source 13 and the receiver 11 can be less than 20 mm.

An electrical current in the method, between a cathode and an anode of the source 13, to record a single image of the tooth 16, can be less than 1 milliamp. Patient radiation exposure in the method to record a single image of the tooth 16 can be less than 1 micro sievert (μSv). Radiation exposure in the method of the patient can be less than 15 micro sieverts (μSv) for a full mouth series of x-rays 12 of all of the patient's teeth and adjacent hard tissue (FMX).

The source 13 and the receiver 11 in the method can be supported by, and attached to each other by, a bite holder. The bite holder can extend across a biting surface of the tooth 16 and can hold the source 13 in position on one side of the tooth 16 and the receiver 11 in position on an opposite side of the tooth 16 while x-rays 12 are emitted through the tooth 16 and received by the receiver 11.

The patient in the method can be human, can be animal, or can be a model, such as of a tooth of human or animal.

What is claimed is:

1. A method of taking x-rays of a patient's tooth, the method comprising:
    a. placing an x-ray emission portion of an x-ray source on one side of the tooth inside of a mouth of the patient and an x-ray image receiving portion of an x-ray receiver on an opposite side of the tooth inside the mouth, wherein:
        i. the source or the receiver is between a cheek or lip of the mouth and the tooth; and
        ii. the other of the source or the receiver is on an opposite side of the tooth; and
    b. emitting x-rays from the source through the tooth and onto the receiver.

2. The method of claim 1, wherein:
    a. the source is an x-ray tube; and
    b. electrical power for the x-ray tube is supplied by a battery-powered, portable power supply.

3. The method of claim 1, wherein the tooth includes multiple teeth and the receiver records an image of multiple teeth at one time.

4. The method of claim 1, wherein the source is a side window x-ray tube.

5. The method of claim 1, wherein a distance between the source and the tooth is less than 5 mm.

6. The method of claim 1, wherein a distance between the source and the receiver is less than 20 mm.

7. The method of claim 1, wherein an electrical current between a cathode and an anode of the source to record a single image of the tooth is less than 1 milliamp.

8. The method of claim 1, wherein patient radiation exposure to record a single image of the tooth is less than 1 micro sievert (μSv).

9. The method of claim 1, wherein radiation exposure of the patient is less than 15 micro sieverts (μSv) for a full mouth series of x-rays of all of the patient's teeth and adjacent hard tissue (FMX).

10. The method of claim 1, wherein:
  a. the source and the receiver are supported, and attached to one another, by a bite holder; and
  b. the bite holder extends across a biting surface of the tooth and holds the source in position on one side of the tooth and the receiver in position on an opposite side of the tooth while x-rays are emitted through the tooth and received by the receiver.

11. An x-ray device for dental x-rays, the device comprising:
  a. an x-ray source sized and configured to have at least an x-ray emission portion of the x-ray source disposed in a patient's mouth;
  b. an x-ray receiver sized and configured to have at least an x-ray image receiving portion of the x-ray receiver disposed in the patient's mouth;
  c. a bite holder attached to the x-ray source and to the x-ray receiver such that an x-ray emission window of the x-ray source faces the x-ray image receiving portion of the x-ray receiver; and
  d. a gap created by the bite holder between the x-ray source and the x-ray receiver;
  e. wherein the gap is sized and configured to extend across a tooth in the patient's mouth and to hold the x-ray source on one side of the tooth and the x-ray receiver on an opposite side of the patient's tooth.

12. The device of claim 11, wherein the source is an x-ray tube and electrical power for the x-ray tube is supplied by a battery-powered, portable power supply.

13. The device of claim 12, wherein the power supply is firmly mounted to the x-ray tube.

14. The device of claim 11, wherein the source is a side window x-ray tube.

15. The device of claim 11, wherein a distance between the source and the tooth is less than 5 mm.

16. The device of claim 11, wherein a distance between the source and the receiver is less than 20 mm.

17. The device of claim 11, wherein the source is configured to have a voltage between an anode and a cathode of less than 51 kilovolts.

18. The device of claim 11, wherein the source is configured to have electrical current between a cathode and an anode of the source to record a single image of the tooth of less than 1 milliamp.

19. The device of claim 11, wherein the source is configured to expose the patient, in recording a single image of the tooth, to less than 1 micro sievert (μSv) of radiation.

20. The device of claim 11, wherein the source is configured to expose the patient, in recording a full mouth series of x-rays of all of the patient's teeth and adjacent hard tissue (FMX), to less than 15 micro sieverts.

* * * * *